United States Patent [19]
Larsen et al.

[11] Patent Number: 4,946,997
[45] Date of Patent: Aug. 7, 1990

[54] RACEMIZATION OF A CARBOXYLIC ACID

[75] Inventors: Robert D. Larsen, Monmouth Junction; Paul Reider, Westfield, both of N.J.

[73] Assignee: Merck & Co., Inc., Rahway, N.J.

[21] Appl. No.: 362,638

[22] Filed: Jun. 7, 1989

[51] Int. Cl.$^5$ .............................................. C07B 55/00
[52] U.S. Cl. ..................................... 562/401; 562/496
[58] Field of Search ................................ 562/401, 496

[56] References Cited

U.S. PATENT DOCUMENTS 4,767,880 8/1988 Wullbrandt et al. ................. 560/61

OTHER PUBLICATIONS

Chem. Lett., p. 1432, (1984).
Chem. Ber., 117, pp. 3457 to 3462, (1984).
Angew. Chem. Int. Ed. Eng., 23, pp 162 to 164, (1984).

Primary Examiner—Werren B. Lone
Assistant Examiner—Vera C. Clarke
Attorney, Agent, or Firm—Melvin Winokur; Joseph F. Diprima

[57] ABSTRACT

A process is described for the racemization of an optically active carboxylic acid of structure (I):

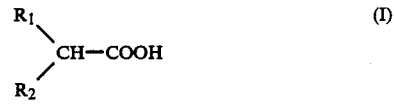

which comprises the treatment of (I) with an acid anhydride and its conjugate base.

8 Claims, No Drawings

RACEMIZATION OF A CARBOXYLIC ACID

BACKGROUND OF THE INVENTION

Pharmacological properties are often dependent on a particular stereochemistry and thus the resolution of a racemic mixture of carboxylic acids is a useful chemical process. However the resolution process besides yielding the desired enantiomer also gives the nondesired enantiomer. It would be desirable in a commercial process to racemize the nondesired enantiomer to a racemic mixture which can then be reemployed in the resolution process.

Ruechardt et al. have reported the racemization of aryl and aryloxycarboxylic acids using acetic anhydride and pyridine, see for example Ruechardt, Gartner and Salz, Chem. Int. Ed. Eng., 23, 162 (1984). It would be beneficial to have a commercially useful racemization procedure that did not employ pyridine and in which the racemizing reagents are employed in catalytic amounts.

DETAILED DESCRIPTION OF THE INVENTION

The present invention is a process for the racemization of an optically active carboxylic acid of structural formula (I); or a mixture enriched therein:

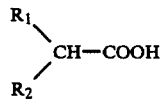

wherein:

$R_1$ and $R_2$ are each independently selected from:
(a) $C_{1-10}$ alkyl optionally substituted with a group X;
(b) $C_{6-10}$ aryl or $C_{7-11}$ araalkyl wherein the aryl moiety is optionally substituted with a group X and optionally contains 1 or 2 heteroatoms such as N, O or S;
(c) $C_{5-8}$ cycloalkyl optionally substituted with X;
(d) $C_{2-10}$ alkenyl optionally substituted with a group X;
(e) $C_{2-10}$ alkynyl optionally substituted with a group X;
(f) $C_{1-5}$ alkyloxy;
(g) $C_{1-5}$ alkylthio;
provided that $R_1$ and $R_2$ are not identical;
X is H, $C_{1-6}$ alkyl, $C_{1-5}$ alkoxy, halogen, $C_{1-5}$ acyloxy, $C_{1-5}$ acylamino, $C_{1-5}$ acyl or trialkylsiloxy.
which comprises: treating (I) which an acid anhydride and the conjugate base of the acid anhydride in an organic solvent.

The groups alkenyl or alkynyl as described herein may be straight or branched chain.

The starting carboxylic acid of formula (I) contains groups $R_1$ and $R_2$ which do not react with the acid anhydride or the conjugate base of the acid anhydride, provided that $R_1$ and $R_2$ are structurally distinct and neither $R_1$ nor $R_2$ is hydrogen. It will be appreciated by those skilled in the art that some substituent groups, such as hydroxy can be contained in $R_1$ or $R_2$ in a protected form such as by formation of a trialkylsilyloxy moiety. The text by T. W. Greene, *Protective Groups in Organic Synthesis* John Wiley & Sons, New York, (1981) describes general methods of protection. $R_1$ and $R_2$ are preferably $C_{1-6}$ alkyl, $C_{6-10}$ or $C_{7-11}$ araalkyl optionally substituted with a group X, or $C_{5-8}$ cycloalkyl optionally substituted with a group X wherein X is $C_{1-6}$ alkyl, $C_{1-5}$ alkoxy, halogen, nitro, $C_{1-5}$ acyloxy, $C_{1-5}$ acyl, $C_{1-5}$ acylamino and trialkyl silyloxy. Further illustrating the groups $R_1$ and $R_2$ are $C_{1-6}$ alkyl, phenyl optionally substituted with X, naphthyl optionally substituted with X, and phenyl $C_{1-3}$ alkyl substituted with X wherein X is $C_{1-6}$ akyl, $C_{1-5}$ alkoxy or nitro.

Specifically exemplifying the carboxylic acid are those compounds (I) wherein:
(a) $R_1$ is 4-isobutylphenyl, $R_2$ is $CH_3$;
(b) $R_1$ is 4-nitrophenyl, $R_2$ is methyl;
(c) $R_1$ is 4-methoxyphenyl, $R_2$ is methyl;
(d) $R_1$ is phenyl, $R_2$ is methyl;
(e) $R_1$ is phenyl, $R_2$ is ethyl;
(f) $R_1$ is 2-(6-methoxynaphthyl), $R_2$ is methyl.

Any acid anhydride and its corresponding conjugate base may be employed provided they do not react with the $R_1$ or $R_2$ moieties. Preferably the acid anhydride/conjugate base is acetic anhydride/sodium acetate or Ibuprofen anhydride/sodium Ibuprofenate.

The organic solvent is a polar solvent selected from isopropyl acetate or hexanes, heptanes toluene, or tetrahydrofuran.

In the present process the carboxylic acid (I) is treated with catalytic amounts of the acid anhydride and the conjugate base of the carboxylic acid at reflux conditions in a polar solvent. The amounts of anhydride/conjugate base are preferably about 10 mole % of that of the carboxylic acid.

EXAMPLE 1

Racemization of S-Ibuprofen

S-Ibuprofen (10.0 g, 48.5 mmol) was dissolved in isopropyl acetate (100 mL) in a 200-mL round-bottomed flask. Acetic anhydride (460 mcL, 4.85 mmol) and sodium acetate (398 mg, 4.85 mmol) were added and the mixture was heated at reflux for 18 hours.

Water (20 mL) was added while the reaction solution was warm.

The solution was cooled and concentrated hydrochloric acid (2 mL) was added.

The layers were separated and the organic layer was washed with water (20 mL) and dried (sodium sulfate). The filtered solution was concentrated to dryness under vacuum. An oil was obtained which crystallized to R/S Ibuprofen after the material was pumped under vacuum.

EXAMPLE 2

Racemization of S-Ibuprofen

Step 1

Preparation of S-Ibuprofen acid chloride (1)

A 500-mL flask fitted with a magnetic stirrer was charged with S-Ibuprofen (20.0 g, 97 mmol) and methylene chloride (200 mL, sieve-dried). The solution was treated with thionyl chloride. (7.8 mL, 106.7 mmol) and dimethylformamide (0.37 mL, 4.85 mmol). This mixture was stirred at room temperature for 4–5 hours.

The solvent was removed under reduced pressure and the residue was pumped under vacuum overnight. The crude acide chloride 1 was obtained wa a light-yellow oil. The material was used directly in the next step without further purification.

Step 2

Preparation of Sodium S-Ibuprofenate (2)

Powdered sodium hydroxide (0.98 g, 24.5 mmol) was dissolved in ethanol-water (99:1, 19.6 mL) with stirring. S-Ibuprofen (5.0 g, 24.4 mmol) was added and the solid was rinsed with ethanol-water (99:1, 5 mL). Once the solid had completely dissolved the solvent was evaporated under reduced pressure. Acetone (50 mL) was added to the residue and this mixture was concentrated to dryness.

The solid was suspended in acetone (50 mL). The solid was filtered, washed with acetone (20 mL), and vacuum dried. The sodium salt 2 was obtained as a white solid. The salt was dried at 50° C. under vacuum to remove moisture from the solid.

Step 3

Racemization of S-Ibuprofen

In a 10-mL round-bottomed flask a mixture of S-Ibuprofen acid chloride (25 mg, 0.11 mmol) and sodium S-Ibuprofenate[1] (50 mg, 0.22 mmol) in isopropyl acetate (5.0 mL) was prepared. The mixture was stirred at room temperature for 2 hours.

[1]This mixture prepares 10 mol% each of Ibuprofen anhydride and sodium Ibuprofenate.

S-Ibuprofen (226 mg, 0.11 mmol) was added and the mixture heated at reflux for 18 hours and worked up as in Example 1.

What is claimed is:

1. A process for the racemization of an optically active acid (I) or a mixture enriched therein:

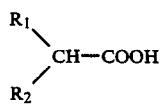
(I)

wherein:

$R_1$ and $R_2$ are each independently selected from:
(a) $C_{1-10}$ alkyl optionally substituted with a group X;
(b) $C_{6-10}$ aryl or $C_{7-11}$ araalkyl wherein the aryl moiety is optionally substituted with a group X and optionally contains 1 to 2 heteroatoms selected from N, O or S;
(c) $C_{5-8}$ cycloalkyl optionally substituted with X;
(d) $C_{2-10}$ alkenyl optionally substituted with a group X;
(e) $C_{2-10}$ alkynyl optionally substituted with a group X;
(f) $C_{1-5}$ alkyloxy;
(g) $C_{1-5}$ alkylthio;
provided that $R_1$ and $R_2$ are not identical;
X is H, $C_{1-6}$ akyl, $C_{1-5}$ alkoxy, halogen, $C_{1-5}$ acyloxy, $C_{1-5}$ acylamino, $C_{1-5}$ acyl, nitro or trialkylsiloxy;
which comprises: treating (I) with an acid anhydride and the conjugate base of the acid anhydride in an organic solvent selected from isopropyl acetate, hexanes, heptanes, toluene, or tetrahydrofuran.

2. A process of claim 1 wherein:
$R_1$ and $R_2$ independently are selected from $C_{1-6}$ alkyl, $C_{6-10}$ aryl, $C_{7-11}$ aralkyl, or $C_{5-8}$ cycloalkyl all substituted with a group X;
X is H, $C_{1-6}$ alkyl, $C_{1-5}$ alkoxy, halogen, nitro, $C_{1-5}$ acyloxy; $C_{1-5}$ acyl, $C_{1-5}$ acylamino, or trialkylsiloxy.

3. A process according to claim 2 wherein $R_1$ and $R_2$ independently are selected from: $C_{1-6}$ alkyl, phenyl, naphthyl or phenyl $C_{1-3}$ alkyl wherein the phenyl or naphthyl moiety is optionally substituted with X;
X is $C_{1-6}$ alkyl, $C_{1-5}$ alkoxy, or nitro.

4. A process according to claim 3 wherein:
$R_1$ is 4-isobutylphenyl and $R_2$ is $CH_3$.

5. A process of claim 4 wherein the acid anhydride is acetic anhydride and the conjugate base is sodium acetate.

6. A process according to claim 4 wherein the acid anhydride is ibuprofen anhydride and the conjugate base is sodium Ibuprofenate.

7. A process according to claim 4 wherein the organic solvent is isopropyl acetate.

8. A process according to claim 4 wherein the amounts of anhydride and conjugate base are approximately 10 mole % of the carboxylic acid (I).

* * * * *